United States Patent [19]

Chou et al.

[11] 4,082,766

[45] Apr. 4, 1978

[54] PROCESS FOR PREPARING N-CHLOROPHTHALIMIDE

[75] Inventors: Ta-Sen Chou; James R. Burgtorf, both of Indianapolis, Ind.

[73] Assignee: Eli Lilly and Company, Indianapolis, Ind.

[21] Appl. No.: 690,471

[22] Filed: May 27, 1976

[51] Int. Cl.$^2$ .................. C07D 209/34; C07D 209/48
[52] U.S. Cl. ............................................. 260/326 HL
[58] Field of Search ................................ 260/326 HL

[56] References Cited

PUBLICATIONS

Zimmer et al., *Journ. Amer. Chem. Soc.*, vol. 76, p. 3856, (1954).
Chem. Abstracts: 7517f (1949).
Chem. Abstracts: vol. 28, 2343$^5$.

*Primary Examiner*—Ethel G. Love
*Attorney, Agent, or Firm*—William C. Martens, Jr.; Everet F. Smith

[57] ABSTRACT

N-Chlorophthalimide is prepared by contacting an alkali metal salt of phthalimide with chlorine under substantially non-aqueous conditions in the presence of a halogenated aliphatic hydrocarbon and at a temperature of from about −10° C. to about +40° C.

9 Claims, No Drawings

PROCESS FOR PREPARING N-CHLOROPHTHALIMIDE

BACKGROUND AND SUMMARY OF THE INVENTION

This invention relates to a process for the manufacture of N-chlorophthalimide. The prior art processes for preparing N-haloimide compounds, and, specifically, N-chloroimide compounds, customarily involve the use of an aqueous system. In general, prior art processess for preparing N-chloroimides can be classified as follows:

(1) Chlorination of the corresponding imide using an inorganic hypochlorite in a mixture of acetic acid and water;

(2) Chlorination by passing chlorine into an aqueous solution comprising equivalent amounts of the corresponding imide and a strong base, e.g., sodium hydroxide or potassium hydroxide;

(3) Chlorination of the corresponding imide using t-butyl hypochlorite in a mixture of t-butyl alcohol and water.

Of the above general methods, only method (2) prescribes the use of chlorine itself in the production of the N-chloroimide. However, due to the fact of the aqueous system, this method has been found to have serious drawbacks. First, chlorine is only very slightly soluble in water. Secondly, and more importantly, it is known that an imide, when present in an alkaline aqueous medium such as would result from potassium or sodium hydroxide and water, undergoes rapid hydrolysis. When, for example, phthalimide is subjected to alkaline aqueous conditions, the following decomposition sequence occurs:

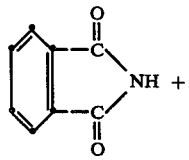

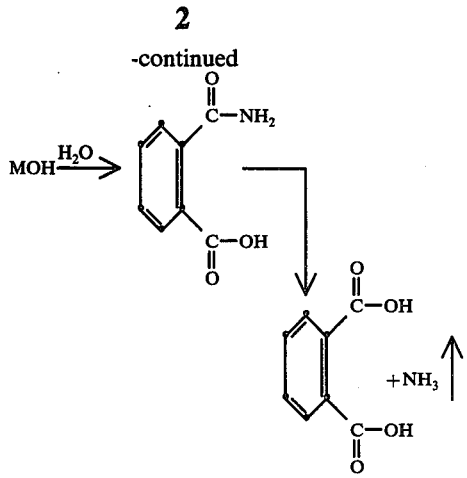

Even more importantly, it has been established [Arthur R. Hurwitz, "Degradation of N-Chlorosuccinimide in Aqueous Solution", Diss. Abst., B, 28 (3), 971 (1967)] that an N-chloroimide product, when present in an aqueous alkaline medium, such as would be the case under the conditions of chlorinations provided by method (2) above, degrades with possible formation of the highly explosive and toxic gas, nitrogen trichloride. The following sequences are postulated for the decomposition of N-chlorosuccinimide:

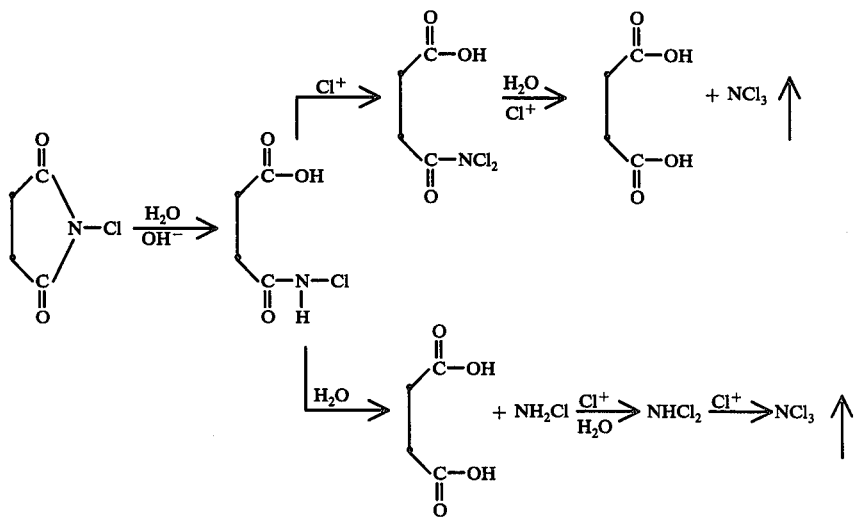

The process of this invention uses molecular chlorine as chlorinating agent and provides the preparation of N-chlorophthalimide both in high yield and high purity and without substantial product degradation due to alkaline hydrolysis. The reaction is carried out in a substantially non-aqueous medium, and the aforementioned deficiencies of an aqueous alkaline medium thus are avoided.

Therefore, this invention is directed to a process for preparing N-chlorophthalimide which comprises contacting an alkali metal salt of phthalimide with chlorine under substantially non-aqueous conditions in the presence of a halogenated aliphatic hydrocarbon and at a temperature of from about −10° C. to about +40° C.

Although the customary prior art methods for preparing N-haloimides are as described above, the literature in an isolated instance does describe a non-aqueous method for preparing N-bromophthalimide. This method, described in J. Bredt and H. Hof, *Berichte*, 33, 21 (1900), involves treating potassium phthalimide with molecular bromine in an inert non-aqueous solvent. The authors describe the method as unsuitable, and they expressly reject this method in favor of the typical prior art method using bromine in an aqueous alkaline medium.

DETAILED DESCRIPTION OF THE INVENTION

As indicated hereinabove, this invention is directed to a process for preparing N-chlorophthalimide. The process of this invention involves the interaction of molecular chlorine with an alkali metal salt of phthalimide in a halogenated aliphatic hydrocarbon and under substantially non-aqueous conditions.

The reaction defined by the process of this invention is equimolar in the sense that one mole of chlorine is consumed for each mole of the alkali metal salt of phthalimide. Therefore, it is highly preferred that an amount of chlorine at least equivalent on a molar basis to the amount of alkali metal salt of phthalimide is employed. Even more preferably, about a 10% excess on a molar basis of chlorine is brought into contact with the alkali metal salt of phthalimide in the selected solvent. The temperature at which the reaction is carried out generally ranges from about $-10°$ C. to about $+40°$ C. and, preferably, from about $-5°$ C. to about $25°$ C. The reaction generally is completed after a period of from about 30 minutes to about 5 hours, and, preferably, is carried out over a period of from about 1 to 2 hours.

The reaction is carried out in the presence of a halogenated aliphatic hydrocarbon. Typical such solvents include methylene chloride, chloroform, carbon tetrachloride, 1,1,2-trichloroethane, 1,2-dichloroethane, 1,1-dichloroethane, 1,1,1-trichloroethane, and the like. The preferred halogenated aliphatic hydrocarbon is methylene chloride.

A further feature of the process of this invention is the carrying out of the reaction under substantially non-aqueous conditions. However, it is not intended by the term "substantially non-aqueous conditions" to mean the total absence of water from the reaction system; instead, this term prescribes the preclusion of any deliberate addition of water to the reaction medium prior to or during the time in which the reaction is being effected. Amounts of water which are customarily present in commercial solvents and reactants need not first be removed in order to comply with the "substantially non-aqueous" requirement.

The alkali metal salts of phthalimide which are intended for use in the process of this invention include the potassium, sodium, and lithium salts. Preferably, the sodium and potassium salts of phthalimide are employed, and, more preferably, the potassium salt of phthalimide is employed in the process of this invention.

Under the conditions presecribed by the process of this invention, the alkali metal salt of phthalimide remains insoluble and thus exists as a slurry in the halogenated aliphatic hydrocarbon solvent. Upon reaction of the alkali metal salt of phthalimide with chlorine, the resulting product, N-chlorophthalimide, dissolves in the reaction mixture. The by-product, the corresponding alkali metal halide, precipitates from the mixture as a white solid.

In general, the reactants are brought into contact at a temperature at the lower end of the contemplated reaction temperature range, for example, at about 0° C., and are allowed to react with warming of the reaction mixture being permitted to occur. The reaction mixture generally is allowed to warm to ambient temperature by removal of any externally applied cooling and is maintained at ambient temperature for the remainder of the reaction period.

A typical and preferred method for carrying out the process of this invention involves the initial preparation of a saturated solution of chlorine in the selected halogenated aliphatic hydrocarbon solvent. The chlorine-saturated hydrocarbon is cooled to a temperature maintained at about $-5°$ C. to about $0°$ C., and the alkali metal salt of phthalimide is added as a solid. The resulting mixture then is stirred and is allowed gradually to warm to ambient temperature. During this period, the alkali metal salt of phthalimide, present as a slurry in the reaction mixture, reacts with the chlorine producing a soluble N-chlorophthalimide and an insoluble alkali metal halide.

Another typical and preferred method for carrying out the process of this invention involves the initial preparation of a slurry of the alkali metal salt of phthalimide in the selected halogenated alaphatic hydrocarbon solvent. The resulting slurry then is brought to the selected temperature of reaction, and a separately prepared solution of chlorine in the selected solvent is added to the slurry. The resulting mixture then is permitted to react in the manner indicated hereinabove. The method by which the chlorine solution is added to the slurry also can be an important factor in the process of this invention. It is preferred that the solution be added as rapidly as possible and that it be added to the slurry by means of an inlet which is positioned below the surface of the reaction medium containing the alkali metal salt of phthalimide.

As noted above, upon completion of the reaction, the reaction mixture will contain the desired product, N-chlorophthalimide, dissolved in the reaction medium and the alkali metal chloride as an insoluble by-product. The desired N-chlorophthalimide can be recovered from the reaction mixture by any of several techniques. One typical method of recovery of the product is, first, to filter the mixture to remove the alkali metal chloride and then to concentrate the filtrate, generally in vacuo, to a volume sufficiently small to effect crystallization of the product upon cooling of the residue. Crystallization of the product can be hastened by the addition of an anti-solvent, such as an aliphatic hydrocarbon, for example, hexane, heptane, and the like.

Alternatively, the product can be recovered from the reaction mixture by first concentrating the mixture with formation of a slurry comprising both the desired N-chlorophthalimide and the alkali metal chloride by-product. To the resulting slurry then is added water which selectively dissolves the alkali metal chloride. The total aqueousorganic mixture then is filtered with collection of the desired N-chlorophthalimide product. When this latter aqueous method of product recovery is employed, it is important to avoid the development of alkaline conditions in the workup. This precludes the possibility of decomposition of the N-chlorophthalimide by the reaction sequences described hereinabove. The N-chlorophthalimide is quite stable under neutral or weakly acidic conditions. Therefore, when the aqueous method of product recovery is employed, the initial aqueous wash can be effected by the use of a weak acid, for example, dilute acetic acid.

The N-chlorophthalimide which is produced by the process of this invention is well recognized as a highly useful reagent for carrying out chlorination reactions which require a source of positive chlorine.

The examples which follow are illustrative of the process of this invention. They are provided solely for the purpose of illustration and are not intended to be limiting on the broad scope of this invention.

EXAMPLE 1

To 325 ml. of cyclohexane-stabilized methylene chloride maintained at 0°–5° C. were added 30 grams (162 mmoles) of potassium phthalimide. Chlorine gas was passed into and below the surface of the resulting rapidly stirred slurry for about 2–3 minutes and until a yellow-green tint persisted. The resulting mixture was stirred for about one hour during which time it was allowed to warm to room temperature. The resulting precipitate then was removed by filtration. The filtrate was evaporated in vacuo to a volume about one-half its original volume, and 200 ml. of n-heptane were added. The resulting mixture was cooled to 0° C., and the crystalline solid was removed by filtration, washed with heptane, and vacuum dried to obtain 12.0 g. (40.7%) of N-chlorophthalimide designated as Crop 1. The filtrate was evaporated to dryness in vacuo to afford 1.4 g. (4.8%) of N-chlorophthalimide designated as Crop 2. The precipitate separated from the initial reaction mixture was slurried in about 350 ml. of water. The remaining insoluble material was collected by filtration, washed with water, and dried in vacuo to afford 14.4 g. (49.0%) of N-chlorophthalimide designated as Crop 3. The total weight yield of product was 94.5%.

| Assay, Available Chlorine — Theory: | 19.6% |
|---|---|
| Crop 1, Found: | 19.2% |
| Crop 2, Found: | 18.0% |
| Crop 3, Found: | 19.3% |

EXAMPLE 2

Chlorine gas was bubbled into one liter of methylene chloride maintained at 0° C. The chlorine was added for about 10 minutes and until saturation was achieved. To the resulting chlorine-saturated methylene chloride were added 50 grams (270 mmoles) of potassium phthalimide as a solid and in one portion. The resulting mixture was allowed to warm gradually to 20° C., and additional chlorine was introduced as a gas during two separate periods to ensure the presence of an excess of chlorine. The mixture then was stirred vigorously at 20° C. for 60–90 minutes. The resulting precipitated potassium chloride was removed by filtration, and the filtrate was evaporated in vacuo to dryness. The residual white solid was suspended in 150 ml. of water for a few minutes, filtered, and washed with 100 ml. of water. The solid was vacuum dried overnight to obtain 44.5 grams (91% yield) of N-chlorophthalimide.

| Assay, Available Chlorine — Theory: | 19.6% |
|---|---|
| Found: | 19.0% |

EXAMPLE 3

To 170 ml. of methylene chloride saturated with chlorine and maintained at 0° C. were added 8.3 grams (49 mmoles) of sodium phthalimide. The resulting mixture was warmed to 20° C. and was stirred for 1.5 hours. The resulting precipitated sodium chloride was removed by filtration, and the filtrate was evaporated to dryness to afford 8.0 grams (90% yield) of N-chlorophthalimide.

| Assay, Available Chlorine — Theory: | 19.6% |
|---|---|
| Found: | 18.7% |

EXAMPLE 4

To 800 ml. of methylene chloride were added 50 grams (270 mmoles) of potassium phthalimide. The resulting slurry was chilled to 0° C. To a jacketed flask maintained immediately above the main reaction vessel were added 200 ml. of methylene chloride. The methylene chloride was saturated with chlorine and was maintained at a temperature of −5° C. to 0° C. The flask containing the chlorinesaturated methylene chloride was equipped with a dry-ice trap to ensure that none of the reagent escaped. The chlorine-saturated methylene chloride then was added to the potassium phthalimide mixture as rapidly as possible by means of a tube which extended below the surface of the potassium phthalimide slurry. Addition was completed in less than 30 seconds. During addition, the temperature of the mixture increased from 0° C. to 10° C. The resulting mixture had a greenish-yellow color which persisted. The mixture was allowed to warm to 20° C. over a two hour period. Some undissolved lumps of potassium phthalimide were noted in the mixture. The resulting potassium chloride percipitate was removed by filtration, and the filtrate was evaporated in vacuo to a slush. Heptane (about 400 ml.) was added, and the mixture was filtered. The collected N-chlorophthalimide was reslurried in about 500 ml. of water and vacuum-dried to afford 42.9 grams (88% yield) of N-chlorophthalimide.

| Assay, Available Chlorine — Theory: | 19.6% |
|---|---|
| Found: | 18.8% |

EXAMPLE 5

Chlorine gas was added to one liter of methylene chloride for 20 minutes at 0° C. during which time saturation was achieved. Potassium phthalimide (50 grams; 270 mmoles) was added to the chlorine-saturated methylene chloride. Cooling was discontinued, and the mixture was stirred for two hours during which time the mixture warmed to 20° C. The resulting slightly greenish-yellow mixture was evaporated to a slush without filtering, and water was added to the mixture to dissolve the resulting potassium chloride. The total mixture was filtered, and the solid which was collected was washed with water and then with heptane. The solid was vacuum-dried overnight to obtain 46.4 grams (95.% yield) of N-chlorophthalimide.

| Assay, Available Chlorine — Theory: | 19.6% |
|---|---|
| Found: | 19.0% |

EXAMPLE 6

The procedure of Example 5 was repeated using 48 grams of potassium phthalimide. The workup was modified to use dilute acetic acid (15.5 ml. glacial acetic acid in 500. m. of water) followed by a water wash. Heptane was not employed. N-chlorophthalimide (42.0 grams; 92.5% yield) was recovered.

| Assay, Available Chlorine — Theory: | 19.6% |
|---|---|
| Found: | 15.8% |

EXAMPLE 7

A. To 100 ml. of carbon tetrachloride saturated with chlorine at 0° C. to 5° C. were added 5 grams (27 mmoles) of potassium phthalimide. The resulting yellow-green suspension was allowed to warm to room temperature and then was stirred for 60–90 minutes. The solvent then was removed in vacuo, and about 100 ml. of water were added to the resulting white solid. The mixture was filtered, and the collected solid was washed with water and vacuum dried to obtain 4.6 grams (94% yield) of N-chlorophthalimide.

| Assay, Available Chlorine — Theory: | 19.6% |
|---|---|
| Found: | 19.4% |

B. The reaction of Part A was repeated using 1,1,2-trichloroethane as solvent to obtain 4.7 grams (96% yield) of N-chlorophthalimide.

| Assay, Available Chlorine — Theory: | 19.6% |
|---|---|
| Found: | 19.0% |

C. The reaction of part A was repeated using 1,2-dichloroethane as solvent to obtain 4.5 grams (92% yield) of N-chlorophthalimide.

| Assay, Available Chlorine — Theory: | 19.6% |
|---|---|
| Found: | 19.1% |

D. The reaction of Part A was repeated using chloroform as solvent. The chloroform was pretreated, first by allowing it to stand over calcium chloride and then by allowing it to stand for 3 days over 4A molecular sieves. N-Chlorophthalimide (4.7 grams; 96% yield) was recovered.

| Assay, Available Chlorine — Theory: | 19.6% |
|---|---|
| Found: | 19.0% |

We claim:

1. A process for preparing N-chlorophthalimide which comprises contacting an alkali metal salt of phthalimide with chlorine under substantially non-aqueous conditions in the presence of a halogenated aliphatic hydrocarbon and at a temperature of from about −10° C. to about +40° C.

2. Process of claim 1, in which the amount of chlorine which is employed is at least equivalent on a molar basis to the amount of the alkali metal salt of phthalimide.

3. Process of claim 1, in which the alkali metal salt of phthalimide is contacted with chlorine at a temperature of from about −5° C. to about 25° C.

4. Process of claim 1, in which the halogenated aliphatic hydrocarbon is methylene chloride.

5. Process of claim 1, in which the alkali metal salt of phthalimide is the sodium or potassium salt of phthalimide.

6. Process of claim 5, in which the alkali metal salt of phthalimide is potassium phthalimide.

7. Process of claim 1, in which the akali metal salt of phthalimide is contacted with chlorine by adding the salt as a solid to the halogenated aliphatic hydrocarbon saturated with chlorine and maintained at a temperature of about −5° C. to about 0° C.

8. Process of claim 1, in which the alkali metal salt of phthalimide is contacted with chlorine by adding a solution of chlorine in said halogenated aliphatic hydrocarbon to a slurry of said alkali metal salt of phthalimide in said halogenated aliphatic hydrocarbon.

9. Process of claim 8, in which the chlorine solution is added by means of an inlet positioned below the surface of said slurry.

* * * * *